(12) United States Patent
Bonk et al.

(10) Patent No.: US 6,203,868 B1
(45) Date of Patent: *Mar. 20, 2001

(54) BARRIER MEMBERS INCLUDING A BARRIER LAYER EMPLOYING POLYESTER POLYOLS

(75) Inventors: Henry W. Bonk, Wallingford, CT (US); David J. Goldwasser, Hillsboro; Paul H. Mitchell, Portland, both of OR (US)

(73) Assignee: Nike, Inc., Beaverton, OR (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/159,210

(22) Filed: Sep. 23, 1998

Related U.S. Application Data

(63) Continuation of application No. 08/475,275, filed on Jun. 7, 1995, now abandoned.

(51) Int. Cl.$^7$ .............................. B32B 27/32; B32B 27/40
(52) U.S. Cl. .................. 428/35.4; 428/36.6; 428/36.7; 428/69; 428/423.1; 428/521
(58) Field of Search ................... 428/35.4, 35.7, 428/36.92, 423.1, 423.3, 424.2, 425.3, 36.6, 36.7, 69, 76, 521, 522

(56) References Cited

U.S. PATENT DOCUMENTS

| | | | |
|---|---|---|---|
| 3,718,494 | 2/1973 | Jacobson | 106/415 |
| 4,082,854 | 4/1978 | Yamada et al. | 426/106 |
| 4,257,176 | 3/1981 | Hartung et al. | 36/44 |
| 4,340,626 | 7/1982 | Rudy | 428/35.7 |
| 4,344,987 | 8/1982 | Ostertag et al. | 427/213 |
| 4,423,185 | 12/1983 | Matsumoto et al. | 525/66 |
| 4,429,076 | 1/1984 | Saito et al. | 525/66 |
| 4,501,790 | 2/1985 | Aizawa et al. | 428/301.1 |
| 4,513,085 | 4/1985 | Martin | 428/336 |
| 4,536,425 | 8/1985 | Hekal | 428/36.4 |
| 4,551,518 | 11/1985 | Matsumoto et al. | 528/80 |
| 4,557,859 | 12/1985 | Maeda et al. | 252/511 |
| 4,610,099 | 9/1986 | Signori | 36/313 |
| 4,614,208 | 9/1986 | Skarelius | 138/103 |
| 4,639,471 | 1/1987 | Hirai et al. | 521/172 |
| 4,681,797 | 7/1987 | Van Iseghem | 428/212 |
| 4,692,361 | 9/1987 | Johnston et al. | 428/35.4 |
| 4,722,131 | 2/1988 | Huang | 29/450 |
| 4,731,289 | 3/1988 | Coleman | 428/334 |
| 4,786,685 | 11/1988 | Takida et al. | 525/58 |

(List continued on next page.)

FOREIGN PATENT DOCUMENTS

| | | |
|---|---|---|
| 2636638 | 3/1990 | (FR) . |
| 52-069486 | 6/1977 | (JP) . |
| 58-22163 | 2/1983 | (JP) . |
| 59-196706 | 11/1984 | (JP) . |
| 59-116145 | 5/1987 | (JP) . |
| 62-253428 | 11/1987 | (JP) . |
| WO 8705563 | 9/1987 | (WO) . |

OTHER PUBLICATIONS

Bayer Polymers Division, Engineering Polymers Properties Guide, Thermoplastics and Thermosets

*Primary Examiner*—Ellis Robinson
*Assistant Examiner*—John J. Figueroa
(74) *Attorney, Agent, or Firm*—Harness, Dickey & Pierce, P.L.C.

(57) ABSTRACT

The present invention relates to barrier membranes including a barrier layer which includes one or more thermoplastic urethane formed from polyester polyols. More particularly, the membranes include a barrier layer including blends of one or more polyester polyol based thermoplastic urethanes and one or more copolymers of ethylene and vinyl alcohol. The barrier membranes can be employed in a variety of applications and can be used as either monolayers or multi-layered laminates.

20 Claims, 7 Drawing Sheets

U.S. PATENT DOCUMENTS

| | | | |
|---|---|---|---|
| 4,865,738 | 9/1989 | Horovitz | 36/29 |
| 4,874,670 | 10/1989 | Boon et al. | 428/423.9 |
| 4,887,367 | 12/1989 | Mackness et al. | 36/28 |
| 4,890,822 | 1/1990 | Ezure et al. | 267/64.23 |
| 4,927,689 | 5/1990 | Markiewicz | 428/3 |
| 4,936,029 | 6/1990 | Rudy | 36/29 |
| 4,960,639 | 10/1990 | Oda et al. | 428/34.5 |
| 4,978,394 | 12/1990 | Ostertag et al. | 106/404 |
| 4,999,229 | 3/1991 | Moritani et al. | 428/36.6 |
| 5,003,002 | 3/1991 | Ofstein | 525/58 |
| 5,030,404 | 7/1991 | Bonnebat et al. | 264/185 |
| 5,036,110 * | 7/1991 | Moureaux | 121/137 |
| 5,036,113 | 7/1991 | Boon et al. | 522/96 |
| 5,036,603 | 8/1991 | Dischler | 36/44 |
| 5,042,176 | 8/1991 | Rudy | 36/29 |
| 5,042,781 | 8/1991 | Ezure et al. | 267/64.23 |
| 5,053,455 | 10/1991 | Kroggel et al. | 525/58 |
| 5,059,245 | 10/1991 | Phillips et al. | 106/31.65 |
| 5,090,010 | 2/1992 | Takahashi | 369/291 |
| 5,096,756 | 3/1992 | Walters | 428/35.5 |
| 5,157,082 | 10/1992 | Johnson | 525/237 |
| 5,198,042 | 3/1993 | Masumoto et al. | 148/403 |
| 5,215,124 | 6/1993 | Hattori et al. | 138/30 |
| 5,246,761 | 9/1993 | Sasaki | 428/156 |
| 5,292,824 | 3/1994 | Nagai et al. | 525/399 |
| 5,300,334 | 4/1994 | Niederst et al. | 428/35.7 |
| 5,332,767 | 7/1994 | Reisser et al. | 523/209 |
| 5,346,950 | 9/1994 | Negi et al. | 525/57 |
| 5,393,832 | 2/1995 | Moulies et al. | 525/57 |
| 5,409,041 | 4/1995 | Yoshida et al. | 138/30 |
| 5,416,988 | 5/1995 | Potter et al. | 36/89 |
| 5,429,852 | 7/1995 | Quinn | 428/71 |
| 5,436,295 | 7/1995 | Nishikawa et al. | 525/92 C |
| 5,456,787 | 10/1995 | Myles | 156/321 |
| 5,458,935 | 10/1995 | Aizner | 428/35.7 |
| 5,462,980 | 10/1995 | Bastioli et al. | 524/47 |
| 5,489,455 | 2/1996 | Nugent, Jr. et al. | 428/36.91 |
| 5,498,662 | 3/1996 | Tanaka et al. | 525/54.2 |
| 5,532,284 | 7/1996 | Barlett et al. | 521/134 |
| 5,540,770 | 7/1996 | Schmid et al. | 106/415 |
| 5,567,489 | 10/1996 | Allen et al. | 428/34.1 |
| 5,578,372 | 11/1996 | Murakami | 428/336 |
| 5,591,798 | 1/1997 | Patel | 524/514 |
| 5,601,889 | 2/1997 | Chundury et al. | 428/34.3 |
| 5,609,962 | 3/1997 | Ouhadi | 428/480 |
| 5,612,101 | 3/1997 | Furuta et al. | 428/357 |
| 5,633,065 | 5/1997 | Matsukura et al. | 428/112 |
| 5,645,923 | 7/1997 | Matsuo et al. | 428/216 |
| 5,662,738 | 9/1997 | Schmid et al. | 106/404 |
| 5,693,424 | 12/1997 | Watanabe et al. | 428/474.7 |
| 5,700,560 | 12/1997 | Kotani et al. | 428/325 |
| 5,713,141 * | 2/1998 | Mitchell et al. | 36/27 |

* cited by examiner

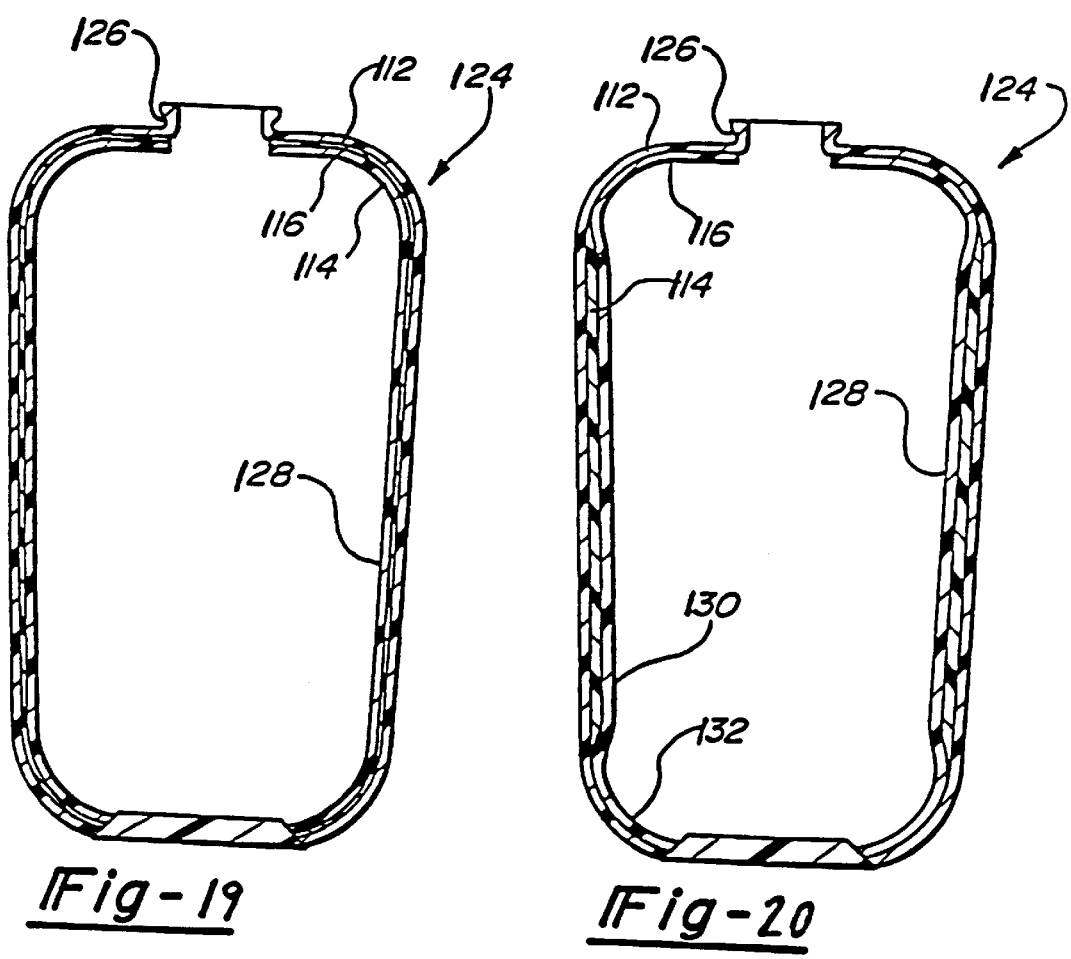

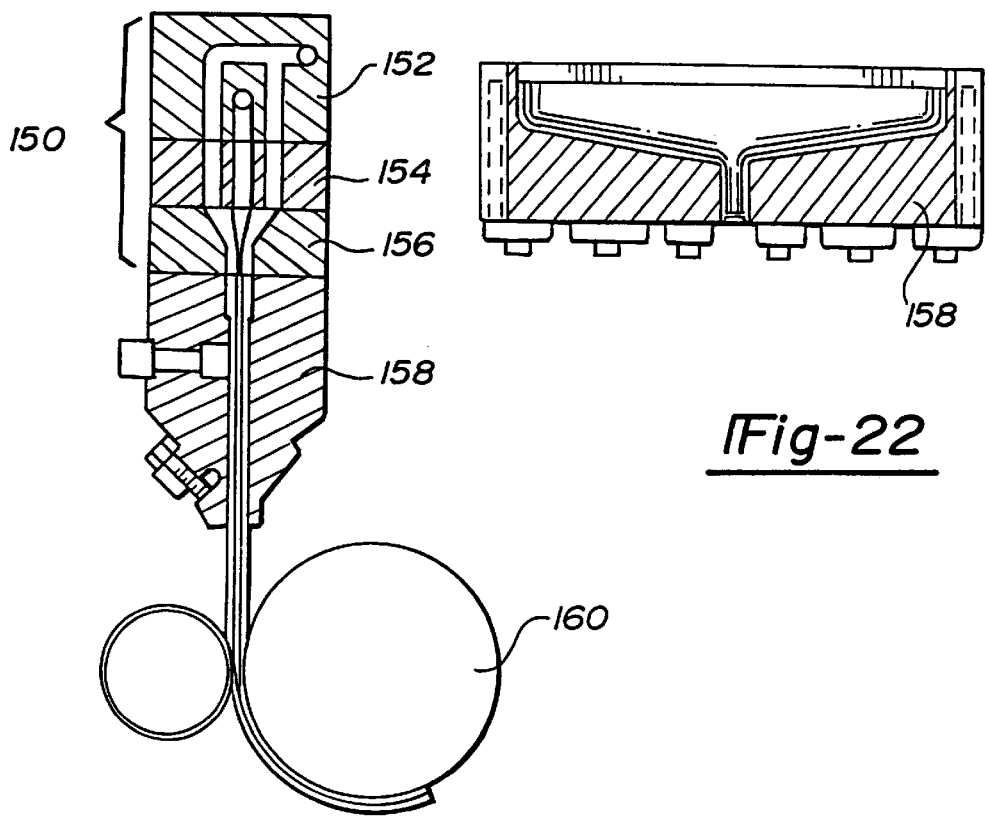
*Fig-22*
*Fig-21*
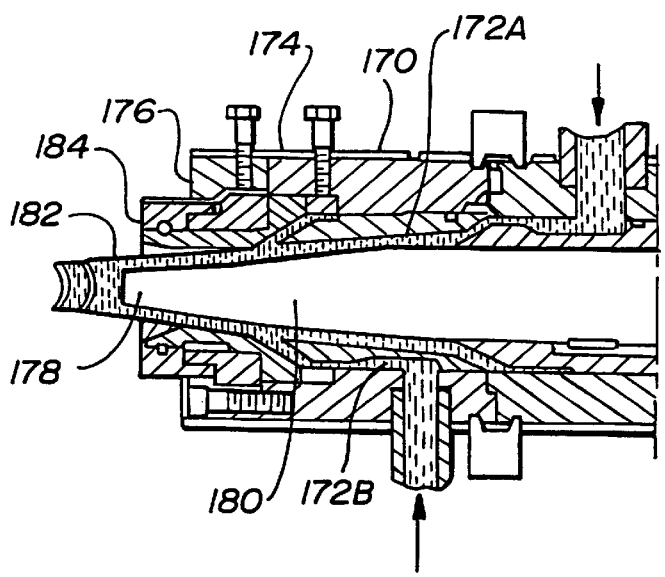
*Fig-23*

BARRIER MEMBERS INCLUDING A BARRIER LAYER EMPLOYING POLYESTER POLYOLS

This application is a continuation of U.S. patent application Ser. No. 08/475,275, filed Jun. 7, 1995, abandoned Sep. 24, 1998.

FIELD OF THE INVENTION

The present invention relates to barrier membranes and, more particularly, to barrier membranes which, under certain embodiments, serve to selectively control the diffusion of gases through the membrane. Additionally, under certain embodiments, the membrane not only selectively controls the diffusion of gases through the membrane, but also allows for the controlled diffusion of gases normally contained in the atmosphere.

For a further understanding of the scope of the present invention, reference can be made to U.S. patent application Ser. No. 08/299,287, entitled "Cushioning Device With Improved Flexible Barrier Membrane" which was filed on Aug. 31, 1994; U.S. patent application Ser. No. 08/299,286 entitled "Laminated Resilient Flexible Barrier Membranes" which was filed on Aug. 31, 1994; and U.S. patent application Ser. No. 08/475,276 filed Jun. 7, 1995, abandoned Aug. 12, 1998, entitled "Barrier Membranes Including A Barrier Layer Employing Aliphatic Thermoplastic Urethanes" which is commonly owned and assigned, and has been filed concurrently herewith; each of the aforementioned patent applications being expressly incorporated herein by reference.

BACKGROUND OF THE INVENTION

Barrier membranes useful for containing fluids, including liquids and/or gases, in a controlled manner, have been employed for years in a wide variety of different products ranging from bladders useful in inflatable objects, including vehicle tires and sporting goods for example; to accumulators used on heavy machinery; to cushioning devices useful in footwear. Regardless of the intended use, desirable barrier membranes must generally be flexible, resistant to environmental degradation and exhibit excellent gas transmission controls. Often, however, materials which exhibit acceptable flexibility characteristics tend to have an unacceptably low level of resistance to gas permeation. In contrast, materials which exhibit an acceptable level of resistance to gas permeation tend to have an unacceptably low level of flexibility.

In an attempt to address the concerns of both flexibility and imperviousness to gases, U.S. Pat. No. 5,036,110 which issued Jun. 30, 1991, to Moreaux describes resilient membranes for fitting hydropneumatic accumulators. According to Moreaux '110, the membrane disclosed consists of a film formed from a graft polymer which is the reaction product of an aromatic thermoplastic polyurethane with a copolymer of ethylene and vinyl alcohol, with this film being sandwiched between layers of thermoplastic polyurethane to form a laminate. While Moreaux '110 attempts to address the concerns in the art relating to flexibility and imperviousness to gases, a perceived drawback of Moreaux is that the film described is not processable utilizing conventional sheet extrusion techniques. Thus, the present invention is directed to barrier membranes which are flexible, have good resistance to gas transmission, and under certain embodiments are processable into laminates utilizing conventional sheet extrusion techniques which are highly resistant to delamination.

While it should be understood by those skilled in the art upon review of the following specification and claims that the barrier membranes of the present invention have a broad range of applications, including but not limited to bladders for inflatable objects such as footballs, basketballs, soccer balls and inner tubes; films for food packaging; as well as the production of fuel lines and fuel storage tanks to name a few, still other applications are possible. For example, one highly desirable application for the barrier membrane of the present invention include their use in forming accumulators which are operable under high pressure environments such as hydraulic accumulators as will be discussed in greater detail below.

For convenience, but without limitation, the barrier membranes of the present invention will hereinafter be described generally in terms of either accumulators or in terms of still another highly desirable application, namely for cushioning devices used in footwear. In order to fully discuss the applicability of the barrier membranes in terms of cushioning devices for footwear, a description of footwear in general is believed to be necessary.

Footwear, or more precisely, shoes generally include two major categories of components namely, a shoe upper and the sole. The general purpose of the shoe upper is to snugly and comfortably enclose the foot. Ideally, the shoe upper should be made from an attractive, highly durable, yet comfortable material or combination of materials. The sole, which also can be made from one or more durable materials, is particularly designed to provide traction, protect the wearer's feet and body during use which Is consistent with the design of the shoe. The considerable forces generated dunng athletic activities require that the sole of an athletic shoe provide enhanced protection and shock absorption for the feet, ankles and legs of the wearer. For example, impacts which occur during running activities can generate forces of up to 2–3 times the body weight of an individual while certain other activities such as, for example, playing basketball have been known to generate forces of up to approximately 6–10 times an individual's body weight. Accordingly, many shoes and, more particularly, many athletic shoes are now provided with some type of resilient, shock-absorbent material or shock-absorbent components to cushion the user during strenuous athletic activity. Such resilient, shock-absorbent materials or components have now commonly come to be referred to in the shoe manufacturing industry as the mid-sole.

It has therefore been a focus of the industry to seek mid-sole designs which achieve an effective impact response in which both adequate shock absorption and resiliency are appropriately taken into account. Such resilient, shock-absorbent materials or components could also be applied to the insole portion of the shoe, which is generally defined as the portion of the shoe upper directly underlining the plantar surface of the foot.

A particular focus in the shoe manufacturing industry has been to seek mid-sole or insert structure designs which are adapted to contain fluids, in either the liquid or gaseous state, or both. Examples of gas-filled structures which are utilized within the soles of shoes are shown in U.S. Pat. No. 900,867 entitled "Cushion for Footwear" which issued Oct. 13, 1908, to Miller; U.S. Pat. No. 1,069,001 entitled "Cushioned Sole and Heel for Shoes" which issued Jul. 29, 1913, to Guy; U.S. Pat. No. 1,304,915 entitled "Pneumatic Insole" which issued May 27, 1919, to Spinney; U.S. Pat. No. 1,514,468 entitled "Arch Cushion" which issued Nov. 4, 1924, to Schopf; U.S. Pat. No. 2,080,469 entitled "Pneumatic Foot Support" which issued May 18, 1937, to Gilbert; U.S. Pat. No. 2,645,865 entitled "Cushioning Insole for Shoes" which issued Jul. 21, 1953, to Towne; U.S. Pat. No. 2,677,906 entitled "Cushioned Inner Sole for Shoes and Method of Making the Same" which issued May 11, 1954, to Reed; U.S. Pat. No. 4,183,156 entitled "Insole Construction for Articles of Footwear" which issued Jan. 15, 1980, to Rudy; U.S. Pat. No. 4,219,945 entitled "Footwear" which issued Sep. 2, 1980, also to Rudy; U.S. Pat. No. 4,722,131 entitled "Air Cushion Shoe Sole" which issued Feb. 2, 1988, to Huang; and U.S. Pat. No. 4,864,738 entitled "Sole Construction for Footwear" which issued Sep. 12, 1989, to Horovitz. As will be recognized by those skilled in the art, such gas filled structures often referred to in the shoe manufacturing industry as "bladders" typically fall into two broad categories, namely (1) "permanently" inflated systems such as those disclosed in U.S. Pat. Nos. 4,183,156 and 4,219,945 and (2) pump and valve adjustable systems as exemplified by U.S. Pat. No. 4,722,131. By way of further example, athletic shoes of the type disclosed in U.S. Pat. No. 4,182,156 which include "permanently" inflated bladders have been successfully sold under the trade mark "AIR SOLE" and other trademarks by Nike, Inc. of Beaverton, Oreg. To date, millions of pairs of athletic shoes of this type have been sold in the United States and throughout the world.

The permanently inflated bladders are typically constructed under methods using a flexible thermoplastic material which is inflated with a large molecule, low solubility coefficient gas otherwise referred to in the industry as a "super gas," such as $SF_6$. By way of example, U.S. Pat. No. 4,340,626 entitled "Diffusion Pumping Apparatus Self-inflating Device" which issued Jul. 20, 1982, to Rudy, which is expressly incorporated herein by reference, discloses a pair of elastomeric, selectively permeable sheets of film which are formed into a bladder and thereafter inflated with a gas or mixture of gases to a prescribed pressure which preferably is above atmospheric pressure. The gas or gases utilized ideally have a relatively low diffusion rate through the selectively permeable bladder to the exterior environment while gases such as nitrogen, oxygen and argon which are contained in the atmosphere and have a relatively high diffusion rate are able to penetrate the bladder. This produces an increase in the total pressure within the bladder, by the addition of the partial pressures of the nitrogen, oxygen and argon from the atmosphere to the partial pressures of the gas or gases contained initially injected into the bladder upon inflation. This concept of a relative one-way addition of gases to enhance the total pressure of the bladder is now known as "diffusion pumping."

Under the diffusion pumping system and depending upon the bladder material used and the choice of gas or gases contained therein, there is a period of time involved before a steady state of internal pressure is achieved. For example, oxygen tends to diffuse into the bladder rather quickly with the effect being an increase in the internal pressure of approximately 2.5 psi. In contrast, over the course of a number of weeks nitrogen gas will gradually diffuse into the bladder resulting in an increase of pressure to approximately 12.0 psi The gradual increase in bladder pressure typically causes an increase in tension in the bladder skin, resulting in a volume increase due to stretching. This effect is commonly referred to in the industry as "tensile relaxation" or "creep." Thus, it is of significant importance which materials are chosen for the bladder and the choice of the captive gas mixture utilized to initially inflate the bladder to achieve a bladder which is essentially permanently inflated at a desired internal pressure and which maintains a desired internal pressure over an extended period of time.

With regard to the systems utilized within the shoe manufacturing industry prior to and shortly after the introduction of the AIR SOLE™ athletic shoes, many of the mid-sole bladders consisted of a single layer gas barrier type films made from polyvinylidene chloride based materials such as SARAN™ (which is a registered trademark of the Dow Chemical Co.) and which by their nature are rigid plastics, having relatively poor flex fatigue, heat sealability and elasticity. Still further, bladder films made under techniques such as laminations and coatings which involve one or more barrier materials in combination with a flexible bladder material (such as various thermoplastics) can potentially present a wide variety of problems to solve. Such difficulties with composite constructions include layer separation, peeling, gas diffusion or capillary action at weld interfaces, low elongation which leads to wrinkling of the inflated product, cloudy appearing finished bladders, reduced puncture resistance and tear strength, resistance to formation via blow-molding and/or heat-sealing and R-F welding, high cost processing, and difficulty with foam encapsulation and adhesive bonding, among others.

Yet another issue with previously known bladders is the use of tie-layers or adhesives in preparing laminates. The use of such tie layers or adhesives generally prevent regrinding and recycling of any waste materials created during product formation back into an usable product, and thus, also contribute to high cost of manufacturing and relative waste. These and other short comings of the prior art are described in more extensive detail in U.S. Pat. Nos. 4,340,626; 4,936,029 and 5,042,176, all of which are hereby expressly incorporated by reference.

With the extensive commercial success of the products such as the AIR SOLE™ shoes, consumers have been able to enjoy a product with a long service life, superior shock absorbency and resiliency, reasonable cost, and inflation stability, without having to resort to pumps and valves. Thus, in light of the significant commercial acceptance and success that has been achieved through the use of long life inflated gas filled bladders, it is highly desirable to develop advancements relating to such products. The goal then is to provide flexible, "permanently" inflated, gas-filled shoe cushioning components which meet, and hopefully exceed, performance achieved by such products as the AIR SOLE™ athletic shoes offered by Nike, Inc.

One key area of potential advancement stems from a recognition that captive gases other than the large molecule, low solubility coefficient "super gases" as described in the '156, '945 and '738 patents utilized can be replaced with less costly and possibly more environmentally friendly gases. For example, U.S. Pat. Nos. 4,936,029 and 5,042,176 specifically discuss the methods of producing a flexible bladder film that essentially maintains permanent inflation through the use of nitrogen as the captive gas. As further described in U.S. Pat. No. 4,906,502, also specifically incorporated herein by reference, many of the perceived problems discussed in the '029 and '176 patents are solved by the incorporation of mechanical barriers of crystalline material into the flexible film such as fabrics, filaments, scrims and meshes. Again, significant commercial success for footwear products using the technology described in '502 patent under the trademark TENSILE AIR™ sold by Nike, Inc. has been achieved. The bladders utilized therein are typically comprised of a thermoplastic urethane laminated to a core fabric three-dimensional, double bar Raschel knit nylon fabric, having $SF_6$ as the captive gas contained therein.

By way of example, an accepted method of measuring the relative permeance, permeability and diffusion of different film materials is set forth in the procedure designated as ASTM D-1434-82. According to ASTM D-1434-82, permeance, permeability and diffusion are measured by the following formulas:

$$\frac{\text{(quantity of gas)}}{\text{(area)} \times \text{(time)} \times \text{(press. diff.)}} = \frac{\text{Permeance}}{\text{Permeance}} = \frac{cc.}{\text{(sq.m)}(24\text{hr})(\text{Pa})}$$

$$\frac{\text{(quantity of gas)} \times \text{(film thick)}}{\text{(area)} \times \text{(time)} \times \text{(press. diff.)}} =$$

$$\frac{\text{Permeability}}{(GTR) \times \text{(film thick)}/\text{(press. diff.)}} = \frac{(cc)(\text{mil})}{\text{(sq.m)}(24\text{hr})(\text{Pa})}$$

$$\frac{\text{(quantity of gas)}}{\text{(area)} \times \text{(time)}} = \frac{\text{Gas Transmission Rate}}{(GTR)} = \frac{cc}{\text{(sq.m)}(24\text{hr})}$$

By utilizing the above listed formulas, the gas transmission rate in combination with a constant pressure differential and the film's thickness, can be utilized to define the movement of gas under specific conditions. In this regard, the preferred gas transmission rate (GTR) for a bladder in an athletic shoe component which seeks to meet the rigorous demands of fatigue resistance imposed by heavy and repeated impacts has a gas transmission rate (GTR) value of approximately 10.0 or lower and, even more preferably, a (GTR) value of 2.0 or lower, for bladders having an average thickness of approximately 20 mils.

In addition to the aforementioned, the '029 and '176 patents also discuss problems encountered with previous attempts to use co-laminated combinations of plastic material which operate as barriers to oxygen. In this regard, the principal concern was the lack of fatigue resistance of the barrier layer. As described in the '176 patent, a satisfactory co-lamination of polyvinylidene chloride (such as SARAN®) and a urethane elastomer would require an intermediate bonding agent. Under such a construction, relatively complicated and expensive processing controls such as strict time-temperature relationships and the use of heated platens and pressures, coupled with a cold press to freeze the materials together under pressure would be required. Additionally, using adhesive tie layers or incorporating crystalline components into the flexible film at high enough levels to accomplish a gas transmission rate of 10 or less, reduces the flexibility of the film.

Cushioning devices which specifically eliminate adhesive tie layers have been known to separate or de-laminate especially along seams and edges. Thus it has been a relatively recent focus of the industry to develop cushioning devices which reduce or eliminate the occurrence of delamination ideally without the use of a "tie layer." In this regard, the cushioning devices disclosed in co-pending U.S. application patent Ser. Nos. 08/299,286 and 08/299,287 eliminate adhesives tie layers by providing membranes including a first layer of thermoplastic urethane and a second layer including a copolymer of ethylene and vinyl alcohol wherein hydrogen bonding occurs over a segment of the membranes between the first and second layers. While the cushioning devices disclosed in U.S. patent application Ser. No. 08/299,287 and the laminated flexible barrier membranes of U.S. patent application Ser. No. 08/299,286 are believed to offer a significant improvement in the art, still further improvements are offered according to the teachings of the present invention.

It is therefore, a principal object of the present invention to provide barrier membranes which offer enhanced flexibility, durability and resistance to the undesired transmission of fluids therethrough.

It is another object of the present invention to provide barrier membranes which can essentially be permanently inflated with nitrogen or another environmentally desirable gas or combination of gases wherein the barrier membrane provides for a gas transmission rate value of 10.0 or less, based on a 20 mils average thickness.

It is still another object of the present invention to provide barrier membranes and, particularly those employed as cushioning devices with improved clarity and consistency.

It is yet another object of the present invention to provide barrier membranes which can be formed into laminated objects such as cushioning devices or accumulators which resist delamination and do not require a tie layer between the barrier layer and the flexible layers It is yet another object of the present invention to provide barrier layers which are reprocessable.

It is a further object of the present invention to provide barrier membranes which are formable utilizing the various techniques including, but not limited to, blow-molding, tubing, sheet extrusion, vacuum-forming, heat-sealing and RF welding.

Still another object of the present invention is to provide barrier membranes which prevent gas from escaping along interfaces between the layers in laminated embodiments and particularly along seems via capillary action.

It is yet another object of the present invention to provide a barrier membrane which allows for normal footwear processing such as encapsulation within a formable material.

While the aforementioned objects provide guidance as to possible applications for the barrier membranes of the present invention, it should be recognized by those skilled in the art that the recited objects are not intended to be exhaustive or limiting.

SUMMARY OF THE INVENTION

To achieve the foregoing objects, the present invention provides barrier membranes which have (1) a desirable level of flexibility (or rigidity); (2) a desirable level of resistance to degradation caused by moisture and (3) an acceptable level of imperviousness to fluids which can be in the form of gases, liquids or both depending mainly on the intended use of the product; and (4) are highly resistant to delamination when employed in a multi-layer structure. Regardless of the barrier membrane embodiment, each barrier membrane in accordance with the teachings of the present invention includes a barrier layer comprised at least in part of a blend of at least one urethane formed from polyester polyols made from combinations of linear dicarboxylic acids and a diol and at least one copolymer of ethylene and vinyl alcohol, wherein the total number of carbons of the combination of dicarboxylic acid(s) and diol(s) is eight or less.

The polyester polyol based urethanes employed, if not commercially available, are generally formed as the reaction product of (a) one or more linear dicarboxylic acids with one or more diols; (b) at least one difunctional extender; (c) at least one isocyanate and/or diisocyanate; and (d) optionally, one or more processing aids.

The term "linear dicarboxylic acid" as used herein preferably means a carboxylic acid having no more than six carbon atoms when reacted with a diol, wherein the reaction product of dicarboxylic acid and diol has no more than eight carbon atoms total.

The term "diol" as used herein is intended to preferably mean polyester diols having no more than six carbon atoms when reacted with a linear dicarboxylic acid, wherein the reaction product of dicarboxylic acid and diol has no more than eight carbon atoms.

The term "polyester diol" as used herein is intended to preferably mean polymeric polyester diols having a molecular weight (determined by the ASTM D-4274 method) falling in the range of about 300 to about 4,000; more preferably from about 400 to about 2,000; and still more preferably between about 500 to about 1,500.

The term "thermoplastic" as used herein preferably is intended to mean that the material is capable of being softened by heating and hardened by cooling through a characteristic temperature range, and as such in the softened state can be shaped into various articles under various techniques.

The term "difunctional extender" is used preferably in the commonly accepted sense to one skilled in the art and includes glycols, diamines, amino alcohols and the like having a molecular weight generally falling in the range of from about 60 to about 300.

Ideally, the flexible barrier materials utilized in accordance with the teachings of the present invention should be capable of containing a captive gas for a relatively long period of time. In a highly preferred embodiment, for example, the barrier membrane should not lose more than about 20% of the initial inflated gas pressure over a period of two years. In other words, products inflated initially to a steady state pressure of between 20.0 to 22.0 psi should retain pressure in the range of about 16.0 to 18.0 psi.

Additionally, the barrier materials utilized should be flexible, relatively soft and compliant and should be highly resistant to fatigue and be capable of being welded to form effective seals typically achieved by RF welding or heat sealing. The barrier material should also have the ability to withstand high cycle loads without failure, especially when the barrier material utilized has a thickness of between about 5 mils to about 50 mils. Another important characteristic of the barrier membrane is that they should be processable into various shapes by techniques used in high volume production. Among these techniques known in the art are extrusion, blow molding, injection molding, vacuum molding, rotary molding, transfer molding and pressure forming. The barrier membranes of the present invention should be preferably formable by extrusion techniques, such as tubing or sheet extrusion, including extrusion blow molding particularly at sufficiently high temperatures to attain the desired "adhesive" or "chemical" bonding as will be described in greater detail below. These aforementioned processes should give rise to products whose cross-sectional dimensions can be varied.

As alluded to above, a significant feature of the barrier membranes of the present invention is the ability under embodiments formed into products intended to be inflated (such as cushioning devices for footwear) to control diffusion of mobile gases through the membrane and to retain the captive gases contained therein. By the present invention, not only are super gases usable as captive gases, but nitrogen gas may also be used as a captive gas due to the performance of the barrier. The practical effect of providing a barrier membrane for which nitrogen gas is a captive gas is significant in terms of protection of the earth's ozone and global warming.

Under the present invention, if the barrier membrane is formed into a product such as a cushioning device, the membrane may be initially inflated with nitrogen gas or a mixture of nitrogen gas and one or more super gases or with air. If filled with nitrogen or a mixture of nitrogen and one or more super gases, an increment of pressure increase results from the relatively rapid diffusion of oxygen gas into the membrane, since the captive gas is essentially retained within the membrane. This effectively amounts to an increase in pressure of not greater than about 2.5 psi over the initial inflation pressure and results in a relatively modest volume growth of the membrane of between 1 to 5%, depending on the initial pressure. However, if air is used as the inflatant gas, oxygen tends to diffuse out of the membrane while the nitrogen is retained as the captive gas. In this instance, the diffusion of oxygen out of the membrane and the retention of the captive gas results in an incremental decrease of the steady state pressure over the initial inflation pressure.

A further feature of the present invention is the enhanced bonding which occurs between contiguous layers, thus, eliminating the need for adhesive tie layers. This is generally accomplished by laminating the first and second layers together using conventional techniques and thus, the laminated barrier membranes of the present invention are characterized in that significant hydrogen bonding occurs between a first layer formed from a blend of at least one aliphatic polyester polyol based urethane and a copolymer of ethylene and vinyl alcohol, and a second layer of thermoplastic urethane. In addition to the occurrence of hydrogen bonding, it is theorized that there will also generally be a certain amount of covalent bonding between the first and second layers, especially when lesser amounts of the copolymer of ethylene and vinyl alcohol is used in the first layer and the thermoplastic urethanes of both the first and second layers have similar functionalities.

Still another feature of the present invention is the excellent gas transmission rates available for monolayer barrier membranes applications of blends of at least one polyester polyol based urethane and a copolymer of ethylene and vinyl alcohol.

This invention has many other advantages which will be more apparent from consideration of the various forms and embodiments of the present invention. Again, while the embodiments shown in the accompanying drawings which form a part of the present specification are illustrative of embodiments employing the barrier membranes of the present invention, it should be clear that the barrier membranes have extensive application possibilities. Various exemplary embodiments will now be described in greater detail for the purpose of illustrating the general principles of the invention, without considering the following detailed description in the limiting sense.

BRIEF DESCRIPTION OF THE DRAWINGS

FIG. 19 is a perspective view of a product formed from a laminated membrane according to the teachings of the present invention;

FIG. 20 is a perspective view of a second product manufactured using a laminated membrane according to the teachings of the present invention;

FIG. 21 is a side elevation view of a sheet co-extrusion assembly;

FIG. 22 is a cross-sectional view of the manifold portion of the sheet co-extrusion assembly of FIG. 22; and FIG. 23 is a side elevation view of a tubing co-extrusion assembly.

DETAILED DESCRIPTION OF THE PREFERRED EMBODIMENTS

Figure 1:
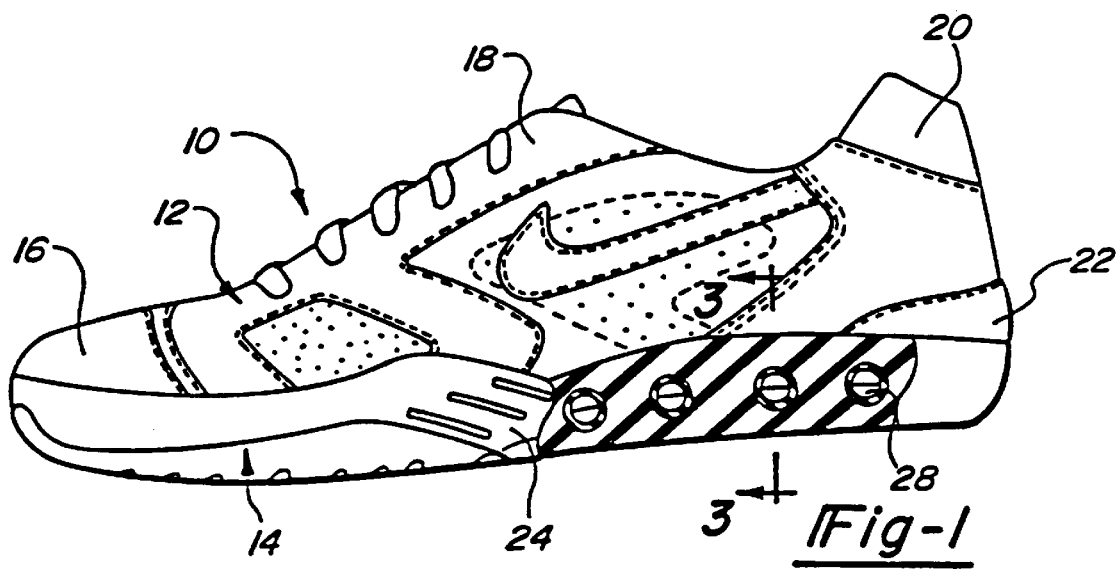
FIG. 1 is a side elevational view of an athletic shoe in accordance with the present invention with a portion of the mid-sole cut-a-way to expose a cross-sectional view.
Figure 2:
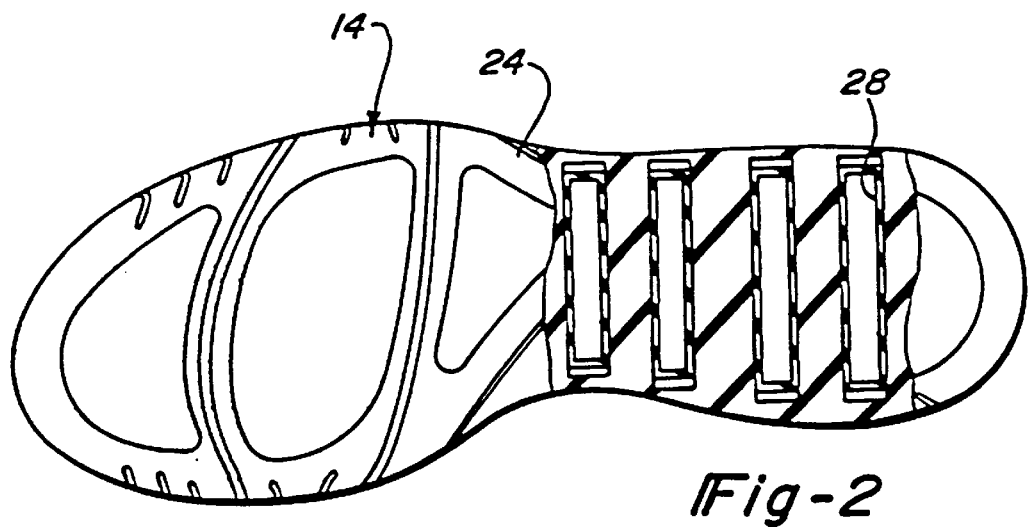
FIG. 2 is a bottom elevational view of the athletic shoe of FIG. 1 with a portion cut-a-way to expose another cross-sectional view.
Figure 3:
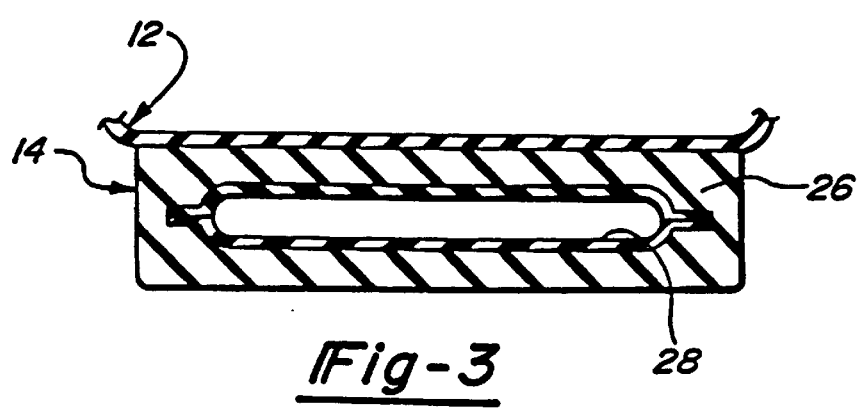
FIG. 3 is a section view taken alone line 3—3 of FIG. 1.
Figure 4:
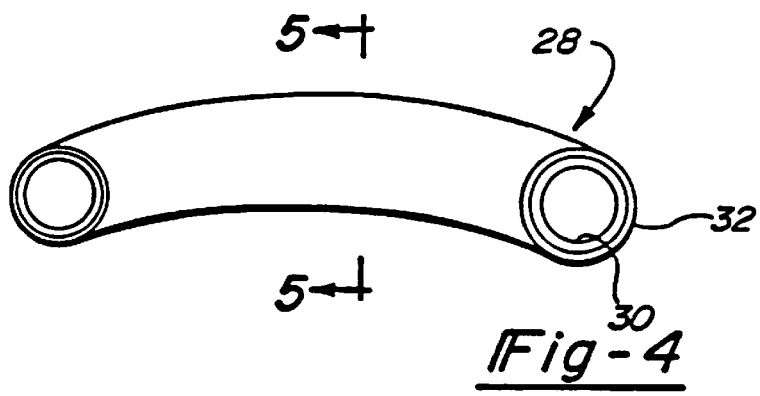
FIG. 4 is a fragmentary side perspective view of one embodiment of a tubular-shaped, two-layer cushioning device in accordance with the present invention.
Figure 5:
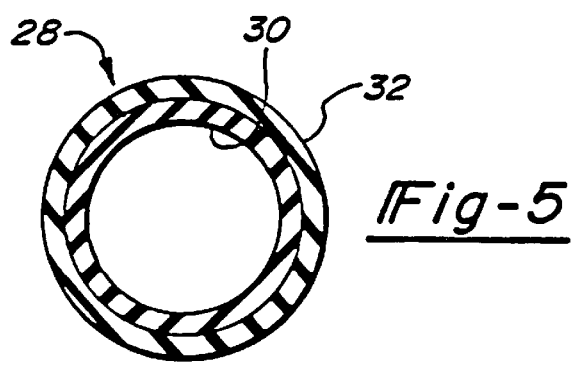
FIG. 5 is a sectional view taken along line 4—4 of FIG. 4.

Referring to FIGS. 1–5, there is shown an athletic shoe, including a sole structure and a cushioning device as one example of a product employing a barrier membrane in accordance with the teachings of the present invention. The shoe 10 includes a shoe upper 12 to which the sole 14 is attached. The shoe upper 12 can be formed from a variety of conventional materials including, but not limited to, leathers, vinyls, nylons and other generally woven fibrous materials. Typically, the shoe upper 12 includes reinforcements located around the toe 16, the lacing eyelets 18, the top of the shoe 20 and along the heel area 22. As with most athletic shoes, the sole 14 extends generally the entire length of the shoe 10 from the toe region 20 through the arch region 24 and back to the heel portion 22.

Figure 8:
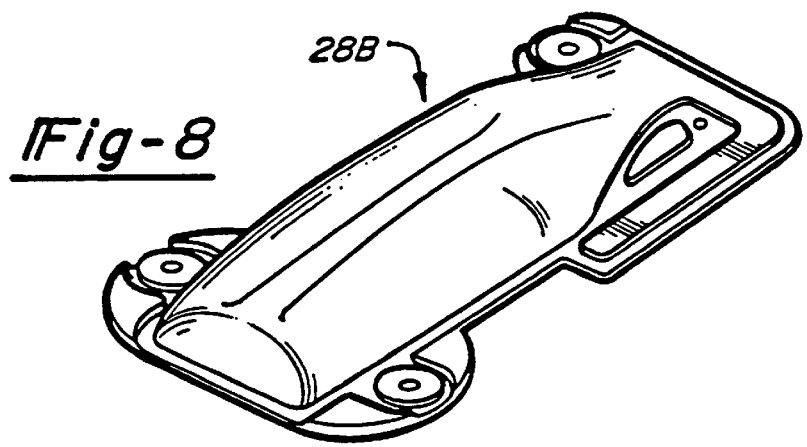
FIG. 8 is a perspective view of an alternative membrane embodiment according to the present invention.
Figure 9:
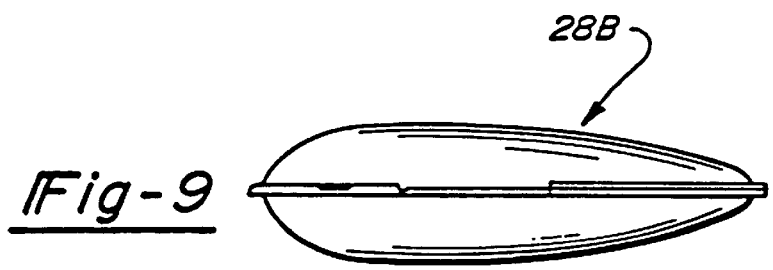
FIG. 9 is a side view of the membrane illustrated in FIG. 8.
Figure 10:
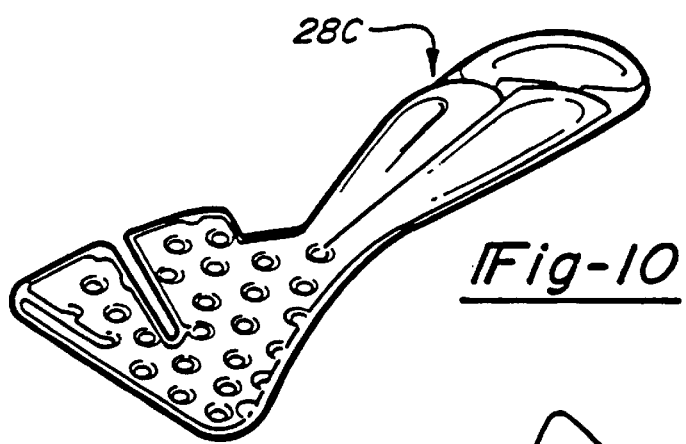
FIG. 10 is a perspective view of an alternative membrane embodiment according to the present invention.
Figure 11:
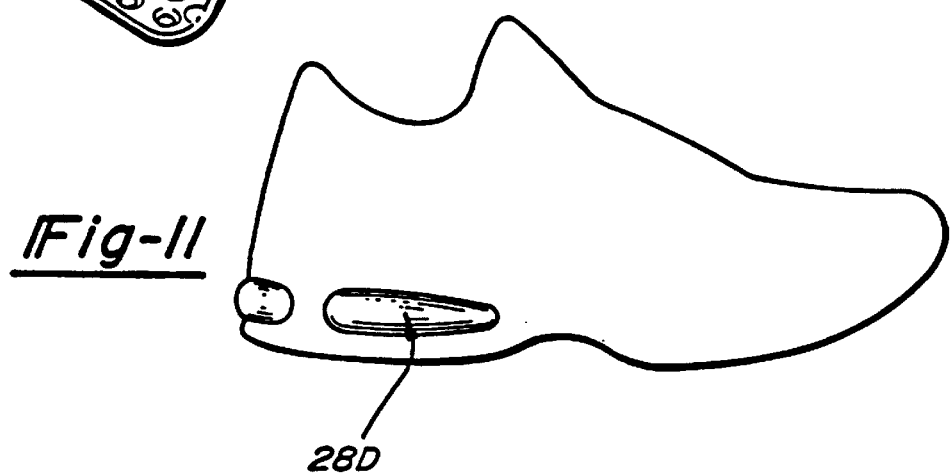
FIG. 11 is a side elevational view of an athletic shoe having an alternative membrane embodiment according to the present invention.
Figure 12:
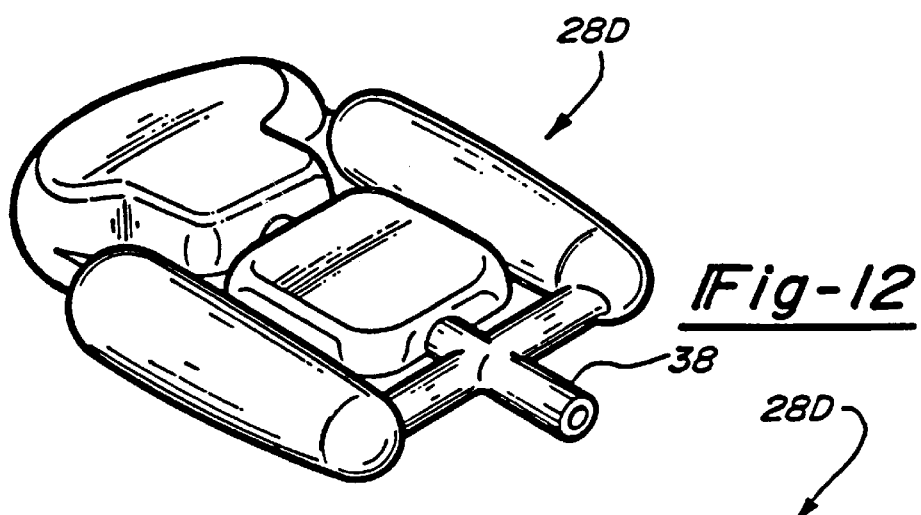
FIG. 12 is a perspective view of the membrane illustrated in FIG. 11.
Figure 13:
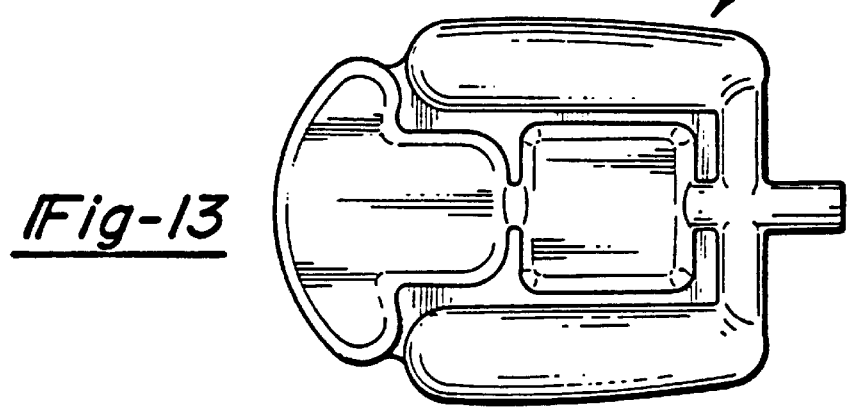
FIG. 13 is a top elevation view of the membrane illustrated in FIGS. 11 and 12.
Figure 14:
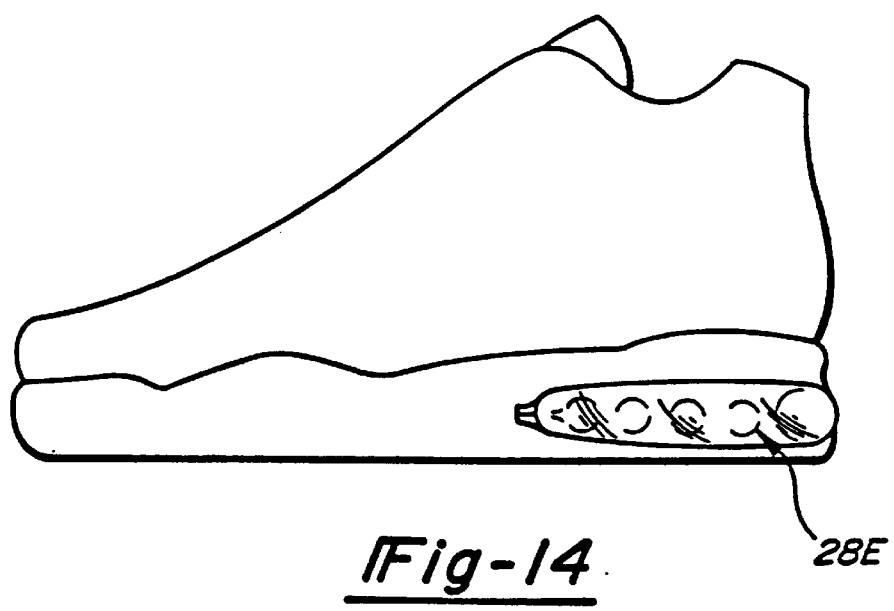
FIG. 14 is a side elevation view of an athletic shoe having another alternative membrane embodiment according to the present invention.
Figure 17:
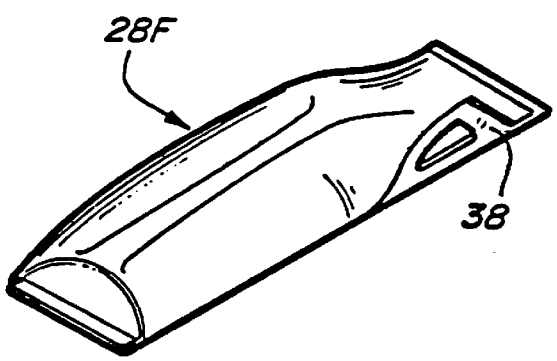
FIG. 17 is a perspective view of an alternative membrane embodiment according to the teachings of the present invention.
Figure 18:
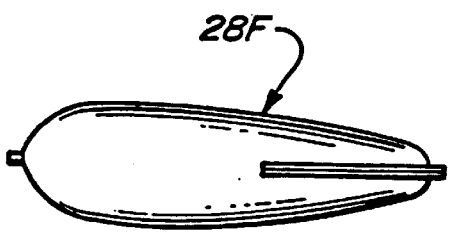
FIG. 18 is a side view of the membrane illustrated in FIG. 17.

The sole structure 14 includes one or more selectively permeable barrier membranes 28 in accordance with the present invention, which are preferably disposed in the mid-sole H of the sole structure. By way of example, the barrier membranes 28 of the present invention can be formed having various geometries such as the plurality of tubular members which are positioned in a spaced apart, parallel relationship to each other within the heel region 22 of the mid sole 26 as illustrated in FIGS. 1–5. The tubular members are sealed to contain an injected captive gas. More specifically, each of the barrier membranes 28 are formed to include a barrier layer which permits diffusion of mobile gases therethrough but which resists or prevents diffusion of the captive gases. These predetermined diffusion properties of the membrane 28 are provided by an inner barrier layer 30 which is disposed along the inner surface of a thermoplastic outer layer 32. These two membrane layers may be best seen in FIGS. 4 and 5. As previously noted, the barrier membranes 28 of the present invention can be formed in a variety of configurations or shapes. For example, alternative membranes 28B could be formed in the shape of a heel ped as illustrated in FIGS. 8 and 9. Athletic shoes including the heel ped configurations set forth in FIGS. 8 and 9 have been used commercially and sold under the trademark AIR HEALT WALKER PLUS™ by Nike, Inc. of Beaverton, Oregon. The heel ped configuration of FIGS. 8 and 9 is also shown in U.S. Design patent application Ser. No. 007,934, filed on Apr. 20, 1993. Similarly, heel peds having a geometry substantially similar to the membrane embodiment 28C illustrated in FIG. 10 have been used in athletic shoes sold under the trademark AIR STRUCTURE II™ by Nike, Inc. The heel ped configuration of FIG. 10 is also shown in U.S. Design Pat. No. 343,504, issued on Jan. 25, 1994. By way of further example, an alternate membrane 28D illustrated with reference to FIGS. 11–13, is currently used in athletic shoes sold under the trademarks AIR MAX$^2$™ and AIR MAX$^2$ CB™, also owned by Nike, Inc. are formable in accordance with the teachings of the present invention. This membrane configuration is also shown in U.S. Design patent No. 349,804, issued on Aug. 23, 1994, and U.S. Design patent No. 350,016 issued on Aug. 30, 1994. Yet, another alternative membrane 28E is illustrated with reference to FIGS. 14–16. The membrane 28E is currently utilized in athletic shoes sold under the trademark AIR MAX™ by Nike, Inc. This membrane configuration is also shown in U.S. Design patent application Ser. No. 897,966, filed on Jun. 12, 1992. Still another membrane configuration designated by reference numeral 28F is illustrated in FIGS. 17 and 18. As should be appreciated by this point, barrier membrane configurations under the present invention (whether in the form of a tube, an elongated ped or other such configuration), may either be fully or partially encapsulated within the mid-sole or out-sole of an article of footwear.

Referring again to FIGS. 1–5, a barrier membrane 28 in accordance with teachings of the present invention is provided in the form of a cushioning device. As shown, the membrane 28 has a composite structure including an outer layer 32 formed of a flexible resilient elastomeric material which preferably is resistant to expansion beyond a predetermined maximum volume for the membrane when subjected to gaseous pressure. The membrane 28 also includes an inner layer 30 formed of a barrier material which allows for controlled diffusion pumping or self-pressurization.

The outer layer 32 preferably is formed of a material or combination of materials which offer superior heat sealing properties, flexural fatigue strength, a suitable modulus of elasticity, tensile and tear strength and abrasion resistance. Among the available materials which offer these characteristics, it has been found that thermoplastic elastomers of the urethane variety, otherwise referred to herein as thermoplastic urethanes or simply TPU's, are highly preferred because of their excellent processibility.

Among the numerous thermoplastic urethanes which are useful in forming the outer layer 32, urethanes such as PELLETHANE™ 2355-85ATP and 2355-95AE (trademarked products of the Dow Chemical Company of Midland, Mich.), ELASTOLLAN® (a registered trademark of the BASF Corporation) and ESTANE® (a registered trademark of the B.F. Goodrich Co.), all of which are either ester or ether based, have proven to be particularly useful. Still other thermoplastic urethanes based on polyesters, polyethers. polycaprolactone and polycarbonate macroglycols can be employed. In general, the thermoplastic urethane (s) employed to form the outer layer 32 will be aromatic in nature.

The inner layer 30, which is the main barrier constituent primarily responsible for controlling gas permeation, is made from a combination or blend of one or more thermoplastic urethanes formed from polyester polyols and one or more copolymers of ethylene and vinyl alcohol. The polyester polyol based thermoplastic urethanes employed in the inner barrier layer, if not commercially available, are generally formed by the reaction product of at least one of each of the following: (a) polyester polyol; (b) difunctional extender; (c) isocyanates and/or diisocyanates; and (d) optionally, processing aids. As previously noted, ideally the polyester polyol is formed as the reaction product of a linear dicarboxylic acid with a diol, wherein the total number of carbon atoms of the reaction product of dicarboxylic acid and diol is eight or less. Under highly preferred embodiments, the polyester polyol employed in barrier layers which are to be formed into laminated membranes will be aliphatic in nature.

Among the linear dicarboxylic acids which are considered to be useful in forming polyester polyol based urethanes under the present invention, those including adipic, glutanic, succinic, malonic and oxylic acids are considered to be particularly useful.

Among the diols which are considered to be useful in accordance with the forming polyester polyol based urethanes under the present invention, those including ethylene glycol, propanediol, butanediol, pentanediol and hexanediol are considered to be particularly useful.

Under highly preferred embodiments, the polyester polyol based thermoplastic urethane employed in forming barrier layers for both monolayer applications and multi-layered laminates, in accordance with the teachings of the present invention will include ethylene glycol adipate. In this regard, certain commercially available ethylene glycol adipates such as FOMREZ® 22-112 and 22-225 available from Witco Chemical are considered to be useful.

Among the difunctional extenders employed in accordance with the teachings of the present inventions are those generally selected from the group consisting of extenders including ethylene glycol, 1,3-propylene glycol, 1,2-propylene glycol, 1,4-butanediol, 1,2-hexanediol, neopentyl glycol, and the like; and dihydroxyalkylated aromatic compounds such as the bis (2-hydroxyethyl) ethers of hydroquinone and resorcinol; p-xylene-α,α'-diol; the bis (2-hydroxyethyl) ether of p-xylene-α,α'-diol; m-xylene-α, α'-diol and the bis (2-hydroxyethyl) ether thereof. Illustrative of diamine extenders are aromatic diamines such as p-phenylenediamine, m-phenylenediamine, benzidine, 4,4'-methylenedianiline, 4,4'-methylenibis (2-chloroaniline) and the like. Illustrative of amino alcohols are ethanolamine, propanolamine, butanolamine, and the like.

Preferred extenders include ethylene glycol, 1,3-propylene glycol, 1,4-butanediol, 1,2-hexanediol, and the like.

Generally, the ratio of polyester polyol (i.e. ethylene glycol adipate) to extender can be varied within a relatively wide range depending largely on the desired hardness of the final polyurethane elastomer. As such, the equivalent proportion of polyester polyol to extender should be within the range of 1:1 to 1:12 and, more preferably, from 1:1 to 1:8.

Among the isocyanates and, more particularly, diisocyanates employed in accordance with the teachings of the present invention, those including isophorone diisocyanate (IPDI), methylene bis 4-cyclohexyl isocyanate, cyclohexyl diisocyanate (CHDI), hexamethylene diisocyanate (HDI), m-tetramethyl xylene diisocyanate (m-TMXDI), p-tetramethyl xylene diisocyanate (P-TMXDI) and xylylene diisocyanate (XDI) are considered to be useful; particularly useful is methylene bis phenyl isocyanate. Generally, the isocyanate(s) employed are proportioned such that the overall ratio of equivalents of isocyanate to equivalents of active hydrogen containing materials is within the range of 0.95:1 to 1.10:1, and preferably 0.98:1 to 1.04:1.

The blended barrier layer 30 will generally include up to 50.0 wt. % polyester polyol based thermoplastic urethane but, more preferably, will include between about 1.0 wt. % to about 30.0 wt. % polyester polyol based thermoplastic urethanes. Under highly preferred embodiments, the polyester polyol based thermoplastic urethane constituency of the barrier layer 30 will be present in the range of between about 5.0 wt. % to about 25.0 wt. %.

Among the copolymers of ethylene and vinyl alcohol employed in the blend forming the barrier layer 30 those including commercially available products such as SOARNOL™ which is available from the Nippon Gohsei Co., Ltd. (U.S.A.) of New York, N.Y., and EVAL® which is available from Eval Company of America, Lisle, Ill. have proven to be useful. Highly preferred commercially available copolymers of ethylene and vinyl alcohol such as EVAL® LCF101A will typically have an average ethylene content of between about 25 mol % to about 48 mol %. In general, higher ethylene contents result in stronger bonding between the respective layers of thermoplastic urethane and ethylene-vinyl alcohol copolymers.

With regard to the use of so-called processing aids, minor amounts of antioxidants, UV stabilizers, mold release agents and non-sticking agents as are known in the art may be employed wherein the total constituency of all such "processing aids" is generally less than 3.0 wt. %.

It may also be desirable to include a catalyst in the reaction mixture to prepare the compositions of the present invention. Any of the catalysts conventionally employed in the art to catalyze the reaction of an isocyanate with a reactive hydrogen containing compound can be employed for this purpose; see, for example, Saunders et al., Polyurethanes, Chemistry and Technology, Part I, Interscience, New York, 1963, pages 228–232; see also, Britain et al., J. Applied Polymer Science, 4, 207–211, 1960. Such catalysts include organic and inorganic acid salts of, and organometallic derivatives of, bismuth, lead, tin, iron, antimony, uranium, cadmium, cobalt, thorium, aluminum, mercury, zinc, nickel, cerium, molybdenum, vanadium, copper, manganese and zirconium, as well as phosphines and tertiary organic amines. Representative organotin catalysts are stannous octoate, stannous oleate, dibutyltin dioctoate, dibutyltin dilaurate, and the like. Representative tertiary organic amine catalysts are triethylamine, triethylenediamine, $N_1N_1N'_1N'$-tetramethylethylenediamine, $N_1N_1N'_1N'$-tetraethylethylenediamine, N-methyl-morpholine, N-ethylmorpholine, $N_1N_1N'_1N'$-tetramethylguanidine, and $N_1N_1N'_1N'$-tetramethyl-1,3-butanediamine.

Regardless of the catalyst(s) which is utilized, if any, the weight percentage of such material is typically less than one half of one percent by weight (0.5 wt. %) based on the total weight of the polyester polyol based thermoplastic urethane reaction mixture.

For certain embodiments, it may also be useful to include a relatively small amount of at least one aromatic thermoplastic urethane in the blended barrier layer 30 as a viscosity modifier. Under those embodiments employing at least one aromatic thermoplastic urethane, the total amount will generally be 3 wt. % or less based on a 100 wt. % constituency of the barrier layer. Thus, the composition of the blended barrier layer can be summarized as including: (1) 50 wt. % to about 97 wt. % of at least one copolymer of ethylene and vinyl alcohol; (2) 3 wt. % to about 50 wt. % of at least one aliphatic thermoplastic urethane; and (3) up to about 3 wt. % of one or more aromatic thermoplastic urethanes, wherein the total constituency of the barrier layer is equal to 100 wt. %. The aromatic thermoplastic urethanes are also selected from the group consisting of polyester, polyether, polycaprolactone, polyoxypropylene and polycarbonate macroglycol based materials and mixtures thereof.

As previously noted, the barrier membranes as disclosed herein can be formed by various processing techniques including but not limited to extrusion, blow molding, injection molding, vacuum molding and heat sealing or RF welding of tubing and sheet extruded film materials. Preferably, all will be described in greater detail below, the membranes of the present invention are made from films formed by co-extruding the outer layer of thermoplastic urethane material and the inner layer of the blended polyester polyol based thermoplastic urethane and copolymer of ethylene and vinyl alcohol together to effectively produce multi-layered film materials with the resulting barrier membranes produced from this material. Subsequently, after forming the multi-layered film materials, the film materials are heat sealed or welded by RF welding to form the inflatable barrier membranes which have the characteristics of both high flexibility and diffusion pumping capabilities.

Figure 6:
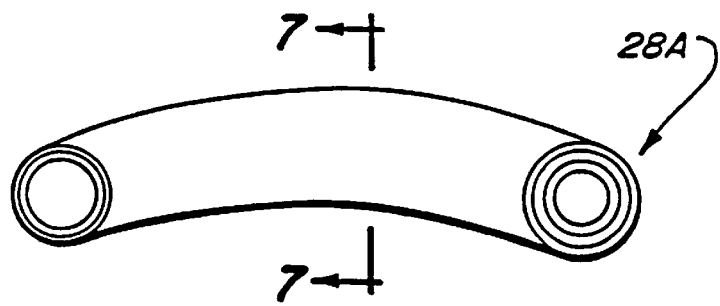
FIG. 6 is a fragmentary side perspective view of a second embodiment of a tubular-shaped, three-layer cushioning device in accordance with the present invention.
Figure 7:
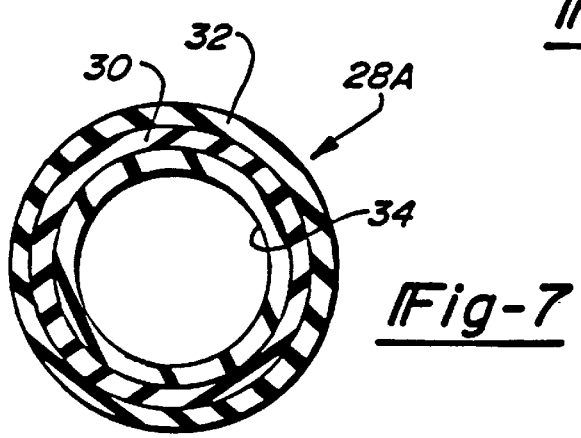
FIG. 7 is a sectional side view taken along line 6—6 of FIG. 6.

Referring now to FIGS. 6 and 7, an alternative barrier membrane embodiment 28A in the form of an elongated tubular shaped multi-layered component is illustrated. The modified barrier membrane 28A is essentially the same as the composite structure illustrated in FIGS. 1–5 except that a third layer 34 is provided contiguously along the inner surface of the barrier layer 30, such that the barrier layer 30 is sandwiched between the outer layer 32 and innermost layer 34. The innermost layer 34 is also preferably made from a thermoplastic urethane material to add further protection against hydrolysis due to moisture for the barrier layer 30. In addition to the benefits of enhanced protection against degradation of the barrier layer 30, layer 34 also tends to assist in providing for high quality welds which allow for the three-dimensional shapes of the cushioning devices.

The cushioning devices shown in FIGS. 1–7 are preferably fabricated from multi-layered extruded tubes. Lengths of the coextruded tubing ranging from one foot to coils of up to 5 feet, are inflated to a desired initial inflation pressure ranging from 0 psi ambient to 100 psi, preferably in the range of 5 to 50 psi, with the captive gas preferably being nitrogen. Sections of the tubing are RF welded or heat sealed to the desired lengths. The individual cushioning devices produced are then separated by cutting through the welded areas between adjacent cushioning devices. It should also be noted that the cushioning devices can be fabricated with so-called lay flat extruded tubing as is known in the art whereby the internal geometry is welded into the tube.

As the blended first layer including the one or more polyester polyol based urethanes and one or more copolymers of ethylene and vinyl alcohol and the second layer including thermoplastic urethane advance to the exit end of the extruder through individual flow channels, once they near the die-lip exit, the melt streams are combined and arranged to float together in layers typically moving in laminar flow as they enter the die body. Ideally, the materials are combined at a temperature of between about 300° F. to about 450° F. and a pressure of at least about 200 psi to obtain optimal wetting for maximum adhesion between the contiguous portions of the layers 30, 32 and 34 respectively. Again, for multi-layered laminates, it is preferred that the polyester polyols utilized in forming the barrier layer be aliphatic in nature, since aliphatic urethanes have been found to be readily processable utilizing conventional sheet extrusion techniques.

As will be discussed in more detail in connection with FIGS. 6 and 7, according to FIGS. 6 and 7, the membrane 28A comprises three layers including a first layer of barrier material 30 sandwiched between second and third layers 32 and 34, respectively, of thermoplastic urethane.

In a highly preferred embodiment, the two thermoplastic urethane layers and the blended barrier layer are coextruded at temperatures sufficient to cause a reactive contact in the form of hydrogen bonding to occur along at least a predetermined segment of the barrier membrane, thus eliminating the need for an intermediate adhesive or bonding layer.

To this end, it is believed that significant bonding occurs as the result of available hydrogen molecules being donated by the vinyl alcohol groups of the ethylene-vinyl alcohol co-polymer along the length of the laminated membrane and hydroxyl and urethane carboxylic groups, or simply the available polar groups of the urethane.

The preferred compositions and methods of the present invention rely exclusively on the inherent properties of the thermoplastic urethane of the second and third layers and the blended barrier layer including the polyester polyol based thermoplastic urethane and one or more copolymers of ethylene and vinyl alcohol when brought into contact according to the methods of the present invention for adhesion.

The theoretical chemical reaction which forms a surface bond between layers 32 and 34 with layer 30 across substantially the entire intended contact surface area of the membrane 28A can be summarized as follows:

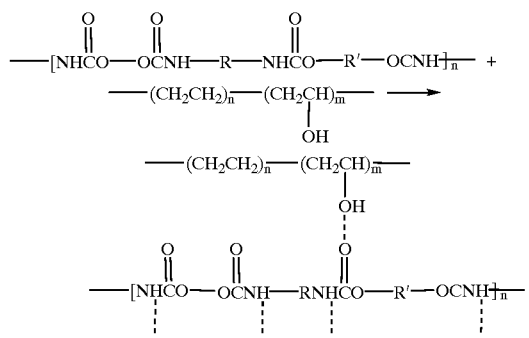

-continued

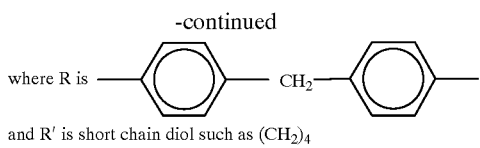

and R' is short chain diol such as $(CH_2)_4$

In addition to the aforementioned theoretical hydrogen bonding, to a more limited extent, it is believed that a certain amount of covalent bonds are formed between the second and third layers 32 and 34, respectively, with the first barrier layer 30. Still other factors such as orientation forces and induction forces, otherwise known as van der Waals forces, which result from London forces existing between any two molecules and dipole-dipole forces which are present between polar molecules are believed to contribute to the bond strength between contiguous layers of thermoplastic urethane and the main barrier layer.

The hydrogen bonding between layers of thermoplastic urethane and the barrier layer of the present invention is in contrast to prior art embodiments which, failing to recognize the existence and/or potential of such bonding, typically have used adhesive tie-layers such as BYNEL®, for example, to improve and maintain the bonding between the various layers of thermoplastic urethane and ethylene vinyl alcohol.

It should also be noted that fillers such as non-polar polymeric materials and inorganic fillers or extenders such as talc, silica, mica, etc., also tend to negatively effect the bonding capacity of the thermoplastic urethane and the blended layer including at least one polyester polyol based urethane and at least one copolymer of ethylene and vinyl alcohol. Thus, the use of fillers in processing the layers 30, 32 and 34 should be extremely limited, if used at all.

Figure 15:
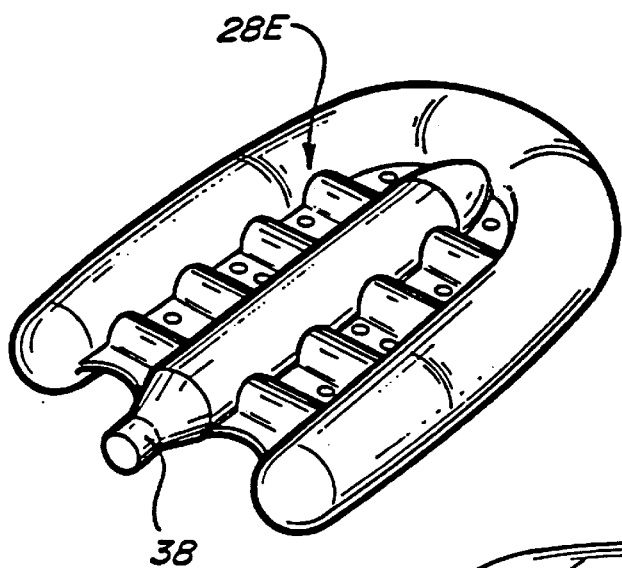
FIG. 15 is a perspective view of the membrane illustrated in FIG. 14.
Figure 16:
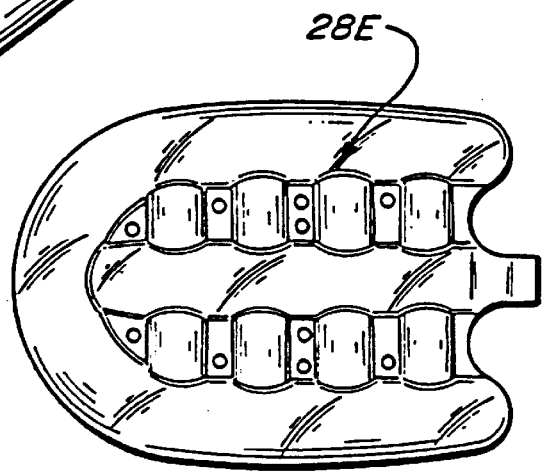
FIG. 16 is a top view of the membrane illustrated in FIGS. 14 and 15.

Referring to FIGS. 12–16, barrier membranes in the form of air bladders, otherwise referred to herein as cushioning devices, which are fabricated by blow molding are shown. To form the air bladders, parisons of two layer, or preferably three layer film are first coextruded as illustrated in FIGS. 21–23, and thereafter, the parisons are blown and formed using conventional blow molding techniques. The resulting bladders, shown best in FIGS. 12 and 15 are then inflated with the desired captive gas to the preferred initial inflation pressure and then the inflation port (e.g. inflation port 38) is sealed by RF welding.

Another air bladder embodiment formed from the barrier membranes described herein is shown in FIGS. 8–10. Sheets or films of coextruded two layer, or preferably three layer film are first formed, with the thickness range of the coextruded sheets or films is generally being between 0.5 mils to 10 mils for the barrier layer 30 and between 5 mils to about 100 mils for the thermoplastic urethane layers 32 and 34, respectively. Two sheets of the multi-layer film are placed on top of each other and welded together along selected points using conventional heat sealing techniques or RF welding techniques. The uninflated bladder is then inflated through a formed inflation port to the desired initial inflation pressure which ranges from 0 psi ambient to 100 psi, and preferably 5 to 50 psi. As previously noted, the preferred captive gas is nitrogen.

Still another air bladder embodiment formed from a barrier membrane of the present invention is shown in FIGS. 17 and 18. The air bladder is fabricated by forming co-extruded two and three layer tubing having a thickness range of the co-extruded tubing wall, i.e. a cross-section through all layers, of between 0.5 mils to about 10 mils for barrier layer 30 and between about 5 mils to about 100 mils for the thermoplastic urethane layers 32 and 34, respectively. The tubing is collapsed to a lay flat configuration and the opposite walls are welded together at selected points and at each end using conventional heat sealing techniques or RF welding. The bladder is then inflated through the formed inflation port 38 to the desired inflation pressure which ranges from 0 psi ambient to 100 psi, and preferably from 5 to 50 psi, with the preferred captive gas being nitrogen.

The various products described and illustrated in the figures are designed to be used as mid-soles for articles of footwear, and particularly in athletic shoes. In such applications, the inflatable membranes may be used in any one of several different embodiments: (1) completely encapsulated in a suitable mid-sole foam; (2) encapsulated only on the top portion of the unit to fill-in and smooth-out the uneven surfaces for added comfort under the foot; (3) encapsulated on the bottom portion to assist attachment of the out-sole; (4) encapsulated on the top and bottom portions but exposing the perimeter sides for cosmetic and marketing reasons; (5) encapsulated on the top and bottom portions but exposing only selected portions of the sides of the unit; (6) encapsulated on the top portion by a molded "Footbed"; and (7) used with no encapsulation foam whatsoever.

In addition to employing the barrier membranes of the present invention as cushioning devices or air bladders as described above, still another highly desirable application for the barrier membranes of the present invention is for accumulators as illustrated in FIGS. 19 and 20.

Referring to FIGS. 19 and 20, there are shown two alternative accumulator embodiments formed from the barrier membrane materials of the present invention. According to FIG. 19, a bladder in the form of a hydraulic accumulator which is used for vehicle suspension systems, vehicle brake systems, industrial hydraulic accumulators or for any accumulators having differential pressures between two potentially dissimilar fluid media is illustrated. The bladder 124 separates the hydraulic accumulator into two chambers or compartments, one of which contains a gas such as nitrogen and the other one of which contains a liquid. Bladder 124 includes an annular collar 126 and a flexible partition 128. Annular collar 126 is adapted to be secured circumferentially to the interior surface of the spherical accumulator such that partition 128 divides the accumulator into two separate chambers. Flexible partition 128 moves generally diametrically within the spherical accumulator and its position at any given time is dependant upon the pressure of the gas on one side in conjunction with the pressure of the liquid on the opposite side.

By way of further example, FIG. 20 illustrates a product manufactured using a combination of the barrier membrane 110, which includes a barrier layer 114 formed from a combination or blend of one or more thermoplastic urethanes formed from polyester polyols and one or more copolymers of ethylene and vinyl alcohol and an outer layer 116 of thermoplastic urethane. It may be desirable to utilize these so-called intermittent constructions under circumstances where the delamination potential along certain segments of a product is generally relatively high. One such location is along the annular collar 128 of bladder or diaphragm for hydraulic accumulators. Thus, it should be recognized that the barrier membranes 110 described herein can include segments which do not include one or more layers of the ethylene vinyl alcohol copolymer.

Preferably, the polyester polyol based thermoplastic urethane and ethylene vinyl alcohol copolymer employed are not modified in an effort to create cross-linking or conventional covalent bonding between the two layers; nor are any tie-layers or adhesive employed. The preferred compositions and methods of the present invention rely exclusively on the inherent properties of the polyester polyol based thermoplastic urethane and copolymer of ethylene and vinyl alcohol when brought into reactive contact according to the methods of the present invention, e.g., to maximize and rely primarily upon hydrogen bonding occurring between the respective layers.

To form the barrier membranes 110 according to the teachings of the present invention, a number of different processes can be used, including but not limited to, coextrusion blow molding utilizing continuous extrusion, intermittent extrusion utilizing (1) reciprocating screw systems, (2) ram accumulator-type systems; (3) and accumulator head systems, coinjection stretch blow molding, or co-extruded sheet, blown film, tubing or profiles. It has been found that multi-layer processes such as tubing, sheet and film extrusion, blow molding utilizing co-extrusions give rise to products which appear to demonstrate the desired significant hydrogen bonding between the respective layers of thermoplastic urethane and the layer(s) including a blend of polyester polyol based thermoplastic urethane and copolymers of ethylene and vinyl alcohol. For example, to form a product such as a hydraulic accumulator bladder or diaphragm via a multi-layer process, such as blow molding a product in accordance with the teachings of the present invention would typically be processed as follows utilizing any one of a number of commercially available blow molding machines such as a Bekum BM502 utilizing a co-extrusion head model no. BKB95-3B1 (not shown) or a Krup KEB-5 utilizing a model no. VW60/35 co-extrusion head (not shown).

A brief description of multi-layer processing techniques will now be provided. Initially, the resinous materials, including the thermoplastic urethanes and the barrier material including a blend of at least one, preferabl aliphatic, polyester polyol based thermoplastic urethane and at least one copolymer of ethylene and vinyl alcohol, are first dried to the manufacturer's specification (if necessary) and fed into the extruder. Typically, the materials are fed into the extruders according to the order in which the layers are to be arranged, for example TPU in an outside extruder, the blend of polyester polyol based TPU and EVOH in a middle extruder and TPU in inside extruder. The extruder heat profile is set for the best processing of the individual materials. However, it is suggested that no more than 20° F. difference be present at the exit point of each extruder. As the material is forced forward in each extruder the heat profile is set to achieve the best molten mass. The heat profile would typically be set for between 300° F. to about 450° F. with the feed zone being the lowest set point and all other set points gradually increasing in increments of approximately 10° F. until the desired melt is achieved. Once leaving the extruders a section of pipes is sometimes used to direct the material to the multi-layered head (i.e. three or more heads). It is at this point that any adjustments for differences in heat be addressed. The pumping action of the extruders not only forces the material into the individual head channels or flow paths but also determines the thickness of each layer. As an example, if the first extruder has a 60 mm diameter, the second has an extruder 35 mm diameter and the third extruder has a 35 mm diameter, the speed required to produce a 1.3 liter bladder or diaphragm requiring 2 mm for the outside layer of TPU, 3 mils for the barrier layer and 2 mm for the inside layer of TPU produced under a desired cycle time of 26 seconds, then the first extruder would have a screw speed of about 10 rpm's, the second extruder would have a screw speed of about 5 rpm's and the third extruder would have a screw speed of about 30 rpm. Once entering the head channels or flow paths, the heat would normally be held constant or be decreased to adjust for the melt strength of the materials. The individual head channels or flow paths keep separate the molten masses while directing them downward and into the shape of a parison.

Just prior to entering the lower die or bushing and the lower mandrel, the material head channels or flow paths are brought together under the pressure created by the now unitary flow path surface area, the gap between the lower bushing and mandrel and the pressure on the individual layers from the respective extruders. This pressure must be at least 200 psi and is normally, under the conditions described, in excess of 800 psi. At the point where the materials come together one parison is now formed that is a laminate made up of the three layers including one layer of thermoplastic urethane, a first layer including a blend of at least one polyester polyol based thermoplastic urethane and at least one copolymer of ethylene and vinyl alcohol, and second and third layers of thermoplastic urethane disposed along opposite sides of the first layer. The upper limit of the pressure is essentially only constrained by the physical strength of the head. After exiting the head, the laminate is closed on each end by the two mold halves and a gas such as air is injected into the mold forcing the laminated parison to blow up against the mold and be held in this fashion until sufficient cooling has taken place (i.e. approximately 16 seconds for the aforementioned sample), at which point the gas is exhausted. The part is then removed from the mold and further cooling is allowed for sufficient time to allow for the part to be de-flashed or further processed as some parts may require. As should now be understood by those skilled in the art, the layers must be held separate until fully melted and preformed into a hollow tube at which time they are chemically bonded as described under the heat and pressure described herein.

As those skilled in the plastic forming industry will recognize, the three major components of a blow molding machine, namely the extruders, die heads and mold clamps, come in a number of different sizes and arrangements to accommodate the consumer production rate schedule and size requirements.

A multi-layer process known as sheet co-extrusion involves an extrusion technique for the simultaneous extrusion of two or more polymers through a single die where the polymers are joined together such that they form distinct, well bonded layers forming a single extruded product. According to the present invention, typical layer structures are defined as follows:

A-B

Two distinct layers consisting of two resins.

A-B-A

Three distinct layers consisting of two or three resins.

A-B-A-B-A

Five distinct layers consisting of two, three, four or five resins.

Wherein A=a layer of thermoplastic urethane and B=at least one layer formed from a resin including a blend of at least one polyester polyol based thermoplastic urethane and at least one copolymer of ethylene and vinyl alcohol.

The equipment required to produce co-extruded sheet consists of one extruder for each type of resin which are connected to a co-extrusion feed block such as that shown in FIGS. 21 and 23, which are commercially available from a number of different sources including the Cloreon Company of Orange, Tex. and Production Components, Inc. of Eau Claire, Wis., among others.

The co-extrusion feed block 150 consists of three sections. The first section 152 is the feed port section which connects to the individual extruders and ports the individual round streams of resin to the programming section 154. The programming section 154 then reforms each stream of resin into a rectangular shape the size of which is in proportion to the individual desired layer thickness. The transition section 156 combines the separate individual rectangular layers into one square port. The melt temperature of the TPU A layers should be between about 300° F. to about 450° F. To optimize adhesion between the TPU A layers and the blended polyester polyol based TPU and EVOH copolymer B layer, the actual temperature of each melt stream should be set such that the viscosities of each melt stream closely match. The combined laminar melt streams are then formed into a single rectangular extruded melt in the sheet die 158 which preferably has a "coat hanger" design as shown in FIG. 22 which is now commonly used in the plastics forming industry Thereafter the extrudate can be cooled utilizing rollers 160 forming a rigid sheet by either the casting or calendaring process.

Similar to sheet extrusion, the equipment required to produce co-extruded tubing consists of one extruder for each type of resin with each extruder being connected to a common multi-manifolded tubing die. The polymer melt from each extruder enters a die manifold such as the one illustrated in FIG. 23 which is commercially available from a number of different sources including Canterberry Engineering, Inc. of Atlanta, Ga. and Genca Corporation of Clearwater, Fla. among others, and flows in separate circular flow channels 172A and 172B for the thermoplastic urethane and the blended polyester polyol based thermoplastic urethane and copolymer of ethylene and vinyl alcohol, respectively. The flow channels are then shaped into a circular annulus the size of which is proportional to the desired thickness for each layer. The individual melts are then combined to form one common melt stream just prior to the die entrance 174. The melt then flows through a channel 176 formed by the annulus between the outer surface 178 of a cylindrical mandrel 180 and the inner surface 182 of a cylindrical die shell 184. The tubular shaped extrudate exits the die shell and then can be cooled into the shape of a tube by many conventional pipe or tubing calibration methods. While a two component tube has been shown in FIG. 23 it should be understood by those skilled in the art that additional layers can be added through separate flow channels.

Regardless of the plastic forming process used, it is of paramount importance that a consistent melt of the resinous thermoplastic urethane, and blended polyester polyol based thermoplastic urethane and copolymer of ethylene vinyl alcohol are obtained to accomplish the desired extensive hydrogen bonding therebetween across the intended length or segment of the laminated product. Thus, the multi-layer processes utilized should be carried out at maintained temperatures of from about 300° F. to about 450° F. for the thermoplastic urethanes and the blend of polyester polyol based thermoplastic urethane and ethylene vinyl alcohol copolymer. Furthermore, it is important to maintain sufficient pressure of at least 200 psi at the point where the layers are joined and hydrogen bonding occurs for a sufficient amount of the hydrogen bonding to be maintained.

As previously noted, in addition to the excellent bonding which is achieved for the laminated barrier membrane embodiments of the present invention, another objective, especially with regard to barrier membranes employed as cushioning devices for footwear, is to provide barrier membranes which are capable of retaining captive gases for extended periods of time. In general, barrier membranes which offer gas transmission rate values of 10.0 or less for a 20 mils thickness as measured according to the procedures designated at ASTM D-1434-82 are acceptable candidates for extended life applications. In this regard, because of the excellent characteristics offered by blends of polyester polyol based urethanes and copolymers of ethylene and vinyl alcohol in terms of flexibility, resistance to degradation caused by moisture and resistance to undesired gas transmissions, among others. The barrier membranes of the present invention can be employed as either multi-layer laminates or single layer constituents of the above described barrier layer materials.

To prepare the non-commercially available samples as set forth in Table I to analyze for gas transmission rate characteristics, the hydroxyl component was initially prepared by adding one or more of the following constituents to a 2000 ml reaction flask: (1) polyester polyol (i.e. commercial product or reaction product of linear dicarboxylic acid and diol, as described); (2) difunctional extender; and (3) processing aids such as waxes and antioxidants. Thereafter, the hydroxyl component was heated to between approximately 95° C.–115° C. (depending on the composition) and stirred to dissolve and homogenize the constituents. Subsequently, a vacuum of less than 0.2 mm Hg was applied under constant stirring to control foaming. After foaming was completed, the flask was degassed for approximately 30 minutes until virtually all bubbling ceased.

Next, the isocyanate component was prepared by disposing a diisocyanate in a 250 ml polypropylene beaker and placing the diisocyanate in an oven heated to between approximately 50–65° C. Upon obtaining a temperature of between about 50–65° C., the desired amount of the isocyanate constituent was weighted out and the catalyst, if any, was added to the isocyanate constituent under constant mixing.

Once the catalyst was fully mixed in, the desired amount of hydroxyl component was added to the isocyanate component to effectuate polymerization. As polymerization began and the viscosity increased (generally between about 7–12 seconds after addition), the reaction product was poured into pans coated with a desirable release agent and allowed to fully cool.

Upon cooling, the newly formed polymer was cut into granules and dried for approximately 2–4 hours at between 85–100° C. Thereafter various samples as set forth in Table I. were cast into sheets to conduct analysis relating to gas transmission properties.

TABLE I*

Gas Transmission Rates For Single Layers

| Formulation | Sample 1 | Sample 2 | Sample 3 | Sample 4 | Sample 5 | Sample 6 | Sample 7 | Sample 8 | Sample 9 | Sample 10 |
|---|---|---|---|---|---|---|---|---|---|---|
| Polybutanediol Adipate | | | | | | | | | | |
| (a) 2000 m.w.[1] | 43.12 | | | | | | | | | |
| (b) 700 m.w.[2] | 15.09 | | | | | | | | | |
| Ethylene Glycol Adipate | | | | | | | | | | |
| (a) 1000 m.w.[3] | | 61.11 | 62.29 | 49.18 | 60.63 | 49.60 | 30.26 | 16.39 | | |
| (b) 500 m.w.[4] | | 61.11 | 62.29 | 49.18 | 60.63 | | 22.69 | 32.77 | | |
| Ethylene Glycol | | | 4.25 | | | | | | | |
| Dipropylene glycol | 0.58 | | | | | | | | | |
| Butyl Carbitol | 0.21 | | | | | | | | | |
| 1,4 Butanediol | 7.37 | 6.05 | | 9.96 | 6.00 | 8.93 | 6.81 | 7.37 | | |
| H12MDI[5] | | | | | | 41.07 | 39.84 | | | |
| MDI[6] | 33.04 | 32.5 | | 40.52 | | | | 43.15 | | |
| MDI/liq. MDI[7] | | | 33.12 | | 33.03 | | | | | |
| Irganaox 1010[8] | 0.125 | 0.15 | 0.15 | 0.15 | 0.15 | 0.15 | 0.15 | 0.15 | | |
| Advawax 280[9] | 0.125 | 0.15 | 0.15 | 0.15 | 0.15 | 0.15 | 0.15 | 0.15 | | |
| Wax[10] | 0.30 | | | | | | | | | |
| Catalyst[11] | 0.04 | 0.04 | 0.04 | 0.04 | 0.04 | 0.10 | 0.10 | 0.02 | | |
| Pellethane 2355-85 ATP[12] | | | | | | | | | 100.0 | |
| Pellethane 2355-95 AE[13] | | | | | | | | | | 100.0 |
| Total Wt. % | 100.0 | 100.0 | 100.0 | 100.0 | 100.0 | 100.0 | 100.0 | 100.0 | 100.0 | 100.0 |

*All values provided in Table I are in weight percents (wt. %)
[1] FOMREZ ™ 44-56 available from Witco Chemical
[2] FOMREZ ™ 44-160 available from Witco Chemical
[3] FOMREZ ™ 22-112 available from Witco Chemical
[4] FOMREZ ™ 22-225 available from Witco Chemical
[5] DESMUDAR W (m.w. 262) available from BAYER AG (America)
[6] ISONATE ™ 125M available from Dow Chemical Co.
[7] Blend of 80 parts IONATE ™ 125M and 20 parts IONATE ™ 143L available from Dow Chemical Co.
[8] IRGANOX ™ 1010 available from Ciba-Gigy Chemical Co.
[9] ADVAWAX ™ 280 available from
[10] Montan ester wax
[11] Blend of 50 parts stannous octoate and 50 parts dioctyl phthalate
[12] PELLETHANE ™ 2355-85 ATP available from Dow Chemical Co.
[13] PELLETHANE ™ 2355-95 AE available from Dow Chemical Co.

TABLE II

| Sample Number | Average Thickness | GTR (cc/m$^2$ * atm * day) | GTR (cc/m$^2$ * atm * day) Normalized to 20 mil thickness |
|---|---|---|---|
| 1 | 16.25 mils | 30.95 | 25.15 |
| 2 | 15.2 mils | 11.71 | 8.9 |
| 3 | 17.13 mils | 9.13 | 7.82 |
| 4 | 18.49 mils | 6.58 | 6.08 |
| 5 | 17.54 mils | 7.07 | 6.19 |
| 6 | 19.93 mils | 9.22 | 9.19 |
| 7 | 19.93 mils | 6.19 | 6.17 |
| 8 | 18.31 mils | 1.20 | 1.10 |
| 9 | 19.95 mils | 36.42 | 36.33 |
| 10 | 18.25 mils | 24.12 | 22.01 | as illustrated in Table II, each of the samples 1–8 demonstrated better gas sion rate results than the control Samples 9–10, which were formed of commercially available thermoplastic urethane resins. Further, Samples 2–8 which relate to polyethylene glycol adipate based urethanes demonstrated better gas transmission rate values than the polybutanediol adipate based urethane of Sample 1.

Since blends employing copolymers of ethylene and vinyl alcohol and polyester polyol based thermoplastic urethanes theoretically have lower gas transmission rates than the polyester polyol based thermoplastic urethanes in and of themselves, Samples 2–8 appear to be excellent candidates for both monolayer and multi-layer barrier membranes, since gas transmission rates values will apparently meet the objective value of 10.0 or less.

While the above detailed description describes the preferred embodiment of the present invention, it should be understood that the present invention is susceptible to modification, variation and alteration without deviating from the scope and fair meaning of the subjoined claims.

What is claimed is:

1. A barrier membrane, comprising:
   a first flexible barrier layer including a blend of at least one copolymer of ethylene and vinyl alcohol and at least one thermoplastic polyurethane, said polyurethane formed from a polyester polyol,
   wherein said barrier membrane is sealed and inflated with a gas toward which said barrier membrane has a transmission rate value of about 10 or less.

2. The barrier membrane according to claim 1, wherein said polyester polyol is a reaction product of (a) a linear dicarboxylic acid having six or less carbon atoms and (b) a diol having six or less carbon atoms, wherein the total number of carbon atoms for the dicarboxylic acid and the diol is eight or less.

3. The barrier membrane according to claim 2, wherein the linear dicarboxylic acid is selected from the group consisting of adipic, glutaric, succinic, malonic and oxalic acids.

4. The barrier membrane according to claim 2, wherein the diol is selected from the group consisting of ethylene glycol, propanediol, butanediol, pentanediol and hexanediol.

5. The barrier membrane according to claim 1, wherein said first layer includes up to about 50 wt. % of thermoplastic polyurethane formed from one or more polyester polyols.

6. The barrier membrane according to claim 5, wherein said first layer includes between about 1 wt. % to about 30 wt. % of thermoplastic polyurethane formed from one or more polyester polyols.

7. The barrier membrane according to claim 6, wherein said first layer includes between about 5 wt. % to about 25 wt. % of thermoplastic polyurethane formed from one or more polyester polyols.

8. The barrier membrane according to claim 1, wherein said copolymer of ethylene and vinyl alcohol is selected from the group consisting of copolymers including an ethylene content of between about 25 mol. % to about 48 mol. %.

9. The barrier membrane according to claim 1, wherein said first layer also includes an aromatic thermoplastic polyurethane.

10. The barrier membrane according to claim 1, wherein said first layer includes:
   (a) 50 wt. % to about 97 wt. % of at least one copolymer of ethylene and vinyl alcohol;
   (b) 3 wt. % to about 50 wt. % of at least one thermoplastic polyurethane formed from a polyester polyol; and
   (c) up to about 3 wt. % of one or more aromatic thermoplastic polyurethanes;
      wherein the total constituency of the first layer equals 100 wt. %.

11. The barrier membrane according to claim 1, further comprising a second layer including a thermoplastic polyurethane which is laminated to said first layer, such that reactive contact in the form of hydrogen bonding occurs along a segment of said barrier membrane between said first and second layers.

12. The barrier membrane according to claim 11, wherein the first layer includes aliphatic polyester polyols.

13. The barrier membrane according to claim 11, wherein said second layer of thermoplastic polyurethane is selected from the group consisting of polyester, polyether, polycaprolactone, polyoxypropylene and polycarbonate macroglycol based materials and mixtures thereof.

14. The barrier membrane according to claim 11, wherein said first layer including a blend of at least one copolymer of ethylene and vinyl alcohol and at least one thermoplastic polyurethane formed from a polyester polyol has an average thickness of between about 0.5 mils to about 10 mils and said second layer of thermoplastic polyurethane has an average thickness of between about 5 mils to about 100 mils.

15. The barrier membrane according to claim 1, wherein said polyester polyol includes ethylene glycol adipate.

16. The laminated barrier membrane according to claim 15, wherein said first layer includes up to about 50 wt. % of thermoplastic urethane formed from one or more polyester polyols.

17. A barrier membrane according to claim 1, wherein said barrier membrane is a three-layer laminate having as a center layer said first barrier layer, a second layer that is an outer layer, and a third layer that is an inner layer.

18. A barrier membrane according to claim 17, wherein at least one of said second and third layers includes a thermoplastic polyurethane.

19. A barrier membrane according to claim 1, wherein the pressure of the inflating gas is between 0 to 100 psi.

20. A barrier membrane according to claim 1, wherein the pressure of the inflating gas is from 5 to 50 psi.

* * * * *

UNITED STATES PATENT AND TRADEMARK OFFICE
CERTIFICATE OF CORRECTION

PATENT NO. : 6,203,868 B1
APPLICATION NO. : 09/159210
DATED : March 20, 2001
INVENTOR(S) : Henry W. Bonk et al.

It is certified that error appears in the above-identified patent and that said Letters Patent is hereby corrected as shown below:

On page 1 of the Title Page, Under References Cited, U.S. PATENT DOCUMENTS, "4,513,085" should be --4,513,058--.

On Page 2 of the Title Page, Under U.S. PATENT DOCUMENTS, "4,865,738" should be --4,864,738--.

On Page 2 of the Title Page, Under U.S. PATENT DOCUMENTS, "5,532,284, 7/1996, Barlett et al." should be --5,532,284, 7/1996, Bartlett et al.--.

Column 2,
Line 30, "Is" should be --is--.
Line 32, "dunng" should be --during--.

Column 3,
Line 58, after "psi" insert --.--.

Column 4,
Line 6, "SARAN$^{TM}$" should be --SARAN®--.

Column 6,
Line 18, after "layers" insert --.--

Column 10,
Line 17, "Healt" should be --Health--.

Column 19,
Line 23, after "industry" insert --.--.

UNITED STATES PATENT AND TRADEMARK OFFICE
CERTIFICATE OF CORRECTION

PATENT NO. : 6,203,868 B1
APPLICATION NO. : 09/159210
DATED : March 20, 2001
INVENTOR(S) : Henry W. Bonk et al.

It is certified that error appears in the above-identified patent and that said Letters Patent is hereby corrected as shown below:

Column 21,
Line 54, "as illustrated" should be --As illustrated--.
Line 55, "gas sion" should be --gas transmission--.

Signed and Sealed this

Twenty-fourth Day of July, 2007

JON W. DUDAS
*Director of the United States Patent and Trademark Office*